US008652075B2

(12) United States Patent
Takahashi et al.

(10) Patent No.: US 8,652,075 B2
(45) Date of Patent: Feb. 18, 2014

(54) WALKING ASSISTANCE DEVICE FOR PROVIDING A WALKING ASSISTANCE FORCE TO A FEMORAL PART OF A USER

(75) Inventors: Hideaki Takahashi, Wako (JP); Taiji Koyama, Wako (JP); Hideo Shimizu, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 194 days.

(21) Appl. No.: 13/127,619

(22) PCT Filed: Oct. 1, 2009

(86) PCT No.: PCT/JP2009/005082

§ 371 (c)(1), (2), (4) Date: May 4, 2011

(87) PCT Pub. No.: WO2010/052824

PCT Pub. Date: May 14, 2010

(65) Prior Publication Data

US 2011/0218466 A1 Sep. 8, 2011

(30) Foreign Application Priority Data

Nov. 6, 2008 (JP) ................................ 2008-285436

(51) Int. Cl.
*A61H 1/00* (2006.01)
*A61F 5/00* (2006.01)

(52) U.S. Cl.
USPC ......... 601/35; 601/5; 601/34; 602/16; 602/23

(58) Field of Classification Search
USPC ........... 601/5, 33, 34, 35, 23, 84, 97–98, 101, 601/104; 602/5, 23, 24, 26, 19
See application file for complete search history.

(56) References Cited

U.S. PATENT DOCUMENTS

| | | | | |
|---|---|---|---|---|
| 3,680,549 | A * | 8/1972 | Lehneis et al. | 602/23 |
| 3,867,930 | A * | 2/1975 | Brown | 602/23 |
| 5,282,460 | A * | 2/1994 | Boldt | 601/5 |
| 5,399,154 | A * | 3/1995 | Kipnis et al. | 602/26 |
| 5,947,916 | A * | 9/1999 | Riedlinger | 602/5 |
| 6,425,166 | B1 * | 7/2002 | Seligman et al. | 24/265 AL |
| 7,001,351 | B2 * | 2/2006 | Reinecke et al. | 602/19 |

(Continued)

FOREIGN PATENT DOCUMENTS

| | | | | |
|---|---|---|---|---|
| EP | 1889592 | A1 * | 2/2008 | A61F 5/01 |
| EP | 1958607 | A1 * | 8/2008 | |

(Continued)

*Primary Examiner* — Justine Yu
*Assistant Examiner* — Christopher Miller
(74) *Attorney, Agent, or Firm* — Rankin, Hill & Clark LLP

(57) ABSTRACT

In a walking assistance device for providing a walking assistance force to a femoral part of a user, the walking assistance force generated by a power generator is effectively transmitted to the femoral part of the user while avoiding the user from experiencing any undue pressure or discomfort. The walking assistance device includes a rigid femoral support frame having a base end connected to an output end of an electric motor unit and a free end extending from the base end to a position opposite to a front part of the femoral part of the user, and a flexible belt attached to the free end of the femoral support frame to be releasably worn around a circumference of the femoral part of the user at a height corresponding to the free end of the femoral support frame.

22 Claims, 5 Drawing Sheets

(56) References Cited

U.S. PATENT DOCUMENTS

| | | | | |
|---|---|---|---|---|
| 7,041,074 | B1 * | 5/2006 | Averianov et al. | 602/20 |
| 7,060,045 | B2 * | 6/2006 | Mason et al. | 602/5 |
| 7,201,728 | B2 * | 4/2007 | Sterling | 602/16 |
| 7,618,386 | B2 * | 11/2009 | Nordt et al. | 602/20 |

FOREIGN PATENT DOCUMENTS

| | | |
|---|---|---|
| JP | 2000-166997 | 6/2000 |
| JP | 2006-320349 | 11/2006 |
| JP | 2006-320350 | 11/2006 |
| JP | 2007-152035 | 6/2007 |

* cited by examiner

WALKING ASSISTANCE DEVICE FOR PROVIDING A WALKING ASSISTANCE FORCE TO A FEMORAL PART OF A USER

TECHNICAL FIELD

This invention relates to a walking assistance device, and in particular to a walking assistance device for providing a walking assistance force to a femoral part of the user thereof.

BACKGROUND OF THE INVENTION

Previously proposed is a walking assistance device for providing a walking assistance force to a femoral part of a user for providing a walking aid or rehabilitation training to the user who may suffer from lack of muscle force (See patent document 1, for instance). This type of walking assistance device comprises a C-shaped pelvic frame configured to be worn on the pelvic part of the user and extending from the lower back part to either side of the pelvic part of the user, a pair of power generators mounted on the parts of the pelvic frame corresponding to either side part of the pelvic part of the user, and a pair of femoral support members for transmitting the assistance force (walking assistance force) of the power generators to the corresponding femoral parts of the user.

Various femoral support members for walking assistance devices have been proposed. One of them includes a rigid semi-cylindrical shell member provided on the free end of an assistance force transmitting arm member, which is drivingly connected to a power generator, so as to surround the outer half (vastus lateralis muscle side) of the femoral part of the user. See patent document 1, for instance. There is also the one including a bifurcated stay member attached to the free end of an assistance force transmitting arm member, which is drivingly connected to a power generator, and a pair of pad members attached to the bifurcated ends of the stay members located ahead of and behind the femoral part of the user to engage the femoral part of the user from the front and back. See patent documents 2 and 3. There is also known the one including an assistance force transmitting arm having a pair of bifurcated free ends which are located ahead of and behind the femoral part of the user and a pair of rigid support plates attached to the free ends of the assistance force transmitting arm so as to engage the femoral part of the user from the front and back via a pad in each case. See patent document 4.

[Patent document 1] JP2000-166997A

[Patent document 2] JP2006-320349A

[Patent document 3] JP2006-320350A

[Patent document 4] JP2007-152035A

BRIEF SUMMARY OF THE INVENTION

Tasks to be Accomplished by the Invention

In the case of the femoral support member using the semi-cylindrical shell member, because the femoral support member is generally made of rigid material, a favorable fit cannot be achieved, and the user is caused to experience pressure and discomfort. In particular, as a rigid member is present behind the femoral part of the user, the user inevitably experiences a significant discomfort when the user tries to sit with the femoral support member on.

When the femoral part of the user is interposed between a pair of pad members from the front and back, as the contact pressure on the femoral part is relatively localized, the walking assistance force cannot be transmitted to the femoral part of the user without causing pressure or discomfort to the user. Furthermore, because of the presence of the rigid support plate on the back side of the femoral part of the user, the user is unable to sit without experiencing some discomfort.

Accordingly, a primary object of the present invention is to provide a walking assistance device for applying a walking assistance force to a femoral part of the user which can effectively transmit a walking assistance force generated by a power generator to the femoral part of the user while avoiding the user from experiencing any undue pressure or discomfort.

Means to Accomplish the Tasks

The present invention provides a walking assistance device for providing a walking assistance force to a femoral part of a user, comprising: a C-shaped pelvic frame configured to be worn on a back part of the user and extending on either side of a pelvic part of the user; a pair of power generators each provided on a part of the pelvic frame corresponding to a corresponding side of the pelvic part of the user; a rigid femoral support frame having a base end connected to an output end of each power generator and a free end extending from the base end to a position opposite to a front part of the femoral part of the user, and a flexible belt attached to the free end of each femoral support frame to be releasably worn around a circumference of the femoral part of the user at a height corresponding to the free end of the femoral support frame.

Preferably, in the walking assistance device of the present invention, the flexible belt is rotatable around a sagittal axis of the user with respect to the free end of the femoral support frame.

In the walking assistance device of the present invention, a part of the free end of the femoral support frame may be provided with a pad member opposite the front part of the femoral part of the user.

In the walking assistance device of the present invention, at least one of the flexible belts and pad members may comprise a surface skin member made of low-friction material.

In the walking assistance device of the present invention, the pad member is rotatable around a sagittal axis of the user with respect to the free end of the femoral support frame.

In the walking assistance device of the present invention, preferably, each femoral support frame is made of a rigid plate having a major surface extending along an outer lateral side of the corresponding femoral part at the base end thereof and along a front side of the corresponding femoral part at the free end thereof so as to form a twisted shape along the outer surface of the femoral part of the user.

In the walking assistance device of the invention, the flexible belt may be at least partly made of elastic material.

Effect of the Invention

According to the walking assistance device of the present invention, the free end of each femoral support frame for transmitting a walking assistance force to the corresponding femoral part of the user is located in front of the femoral part of the user, and the free end of the femoral support frame is secured to the femoral part of the user by using a flexible belt wrapped around the entire circumference of the femoral part at the height of the free end of the femoral support frame so that the walking assistance force generated by the power generator can be accurately transmitted to the femoral part in the direction of the sagittal axis of the user or in the fore and aft direction of the user.

As the flexible belt is wrapped around the entire circumference of the femoral part of the user, the contact pressure between the support member (femoral support frame and flexible belt) and the femoral part can be distributed over a large surface area. Furthermore, because the femoral support frame consisting of a rigid member engages the femoral part only at the rectus femoris muscle in the front part of the femoral part of the user which undergoes a relatively small deformation in walking as compared to the semitendinosus muscle and biceps femoris muscle which are in the rear part of the femoral part of the user, and the semitendinosus muscle and biceps femoris muscle are simply wrapped around by the flexible belt 50L, 50R so that the user is not subjected to any undue pressure or discomfort. Also, as there is no hard member behind the femoral part of the user, the user wearing the walking assistance device can comfortable sit.

Figure 1:
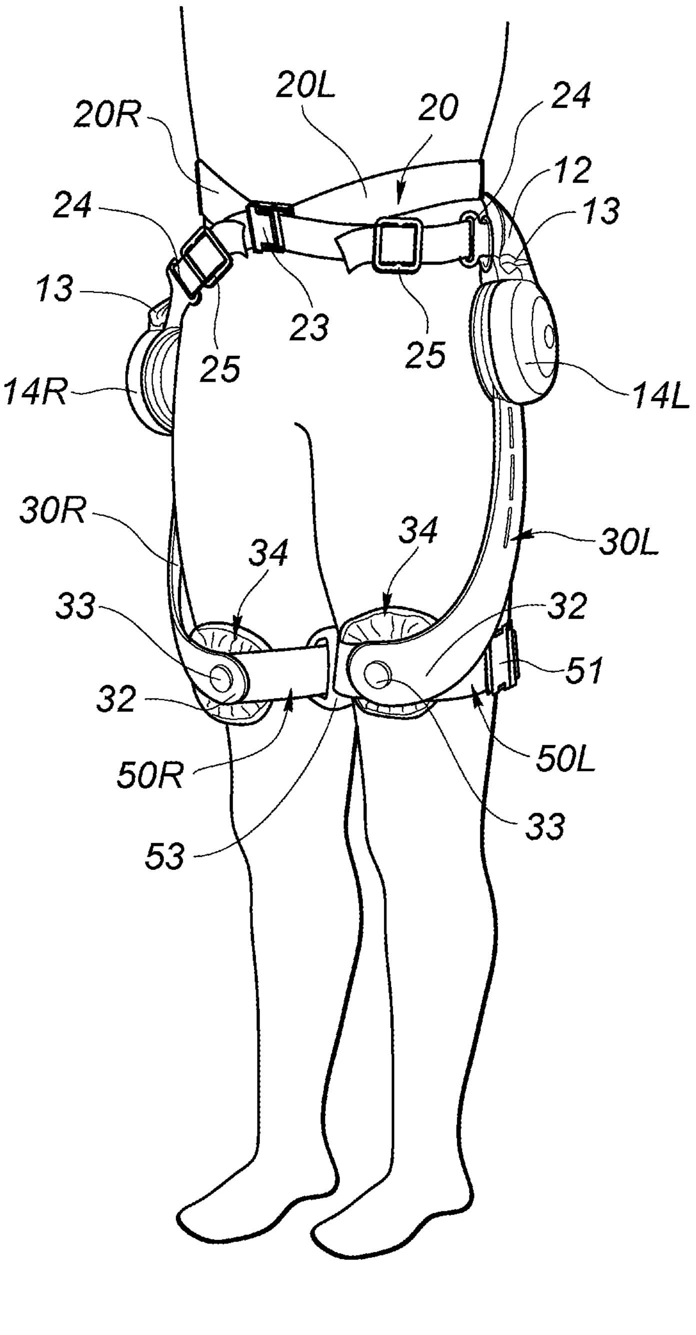
FIG. 1 is a front perspective view showing a walking assistance device embodying the present invention when being worn by the user.
Figure 2:
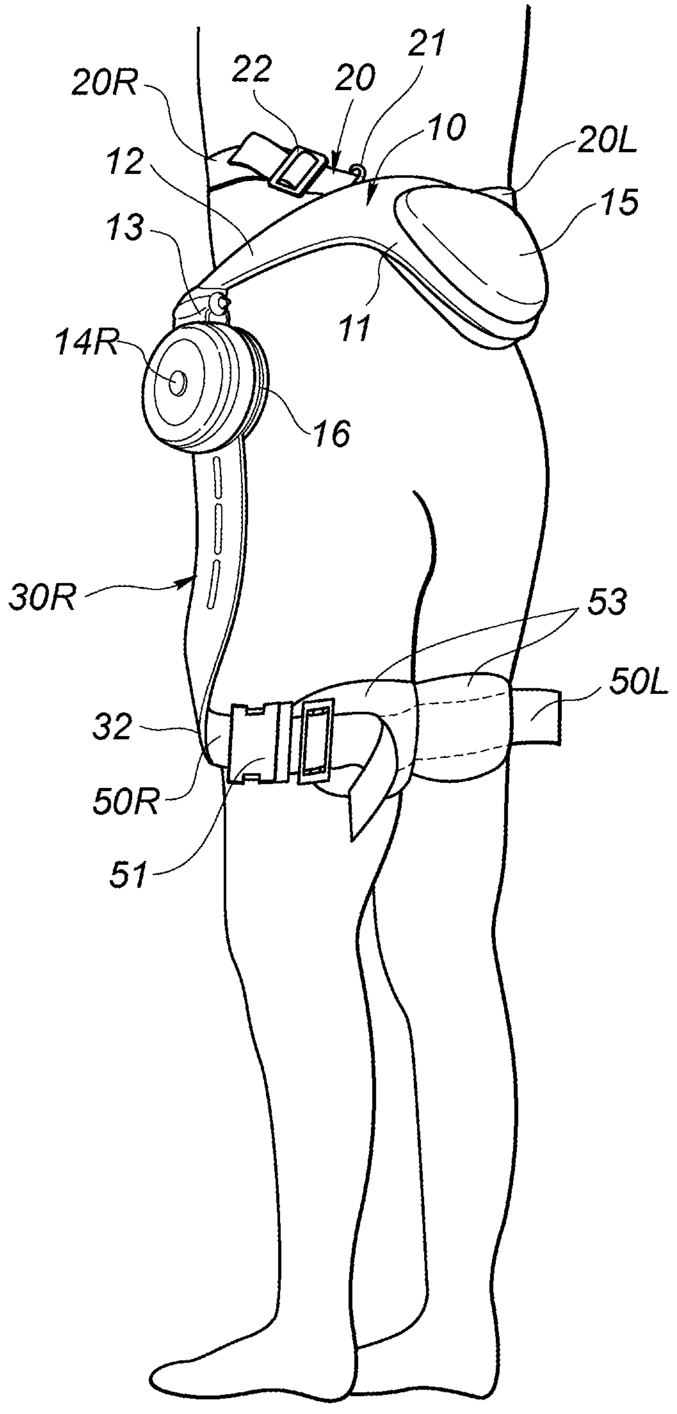
FIG. 2 is a back perspective view of the walking assistance device when being worn by the user.
Figure 3:
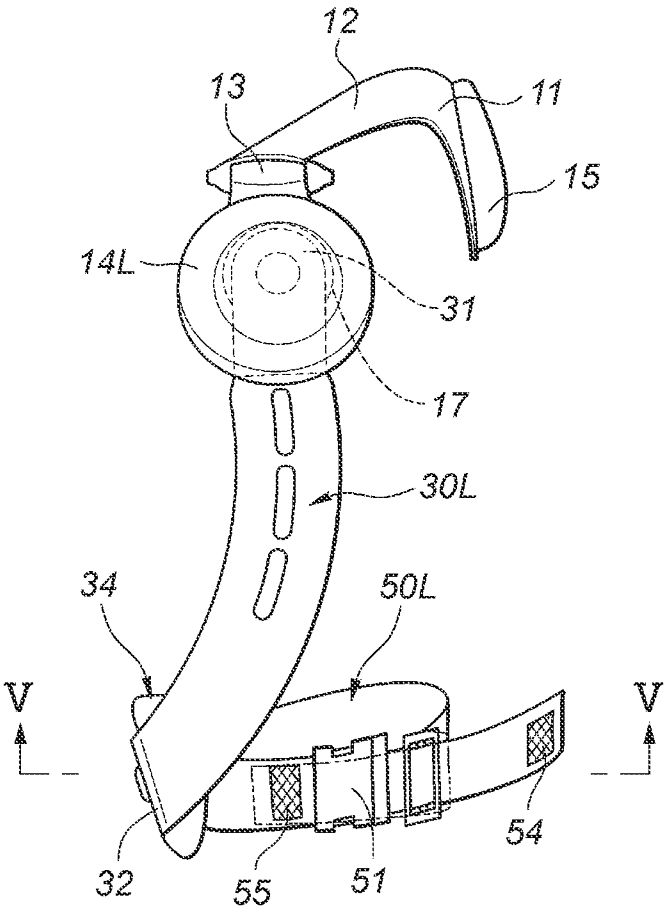
FIG. 3 is a side view of an essential part of the walking assistance device.
Figure 4:
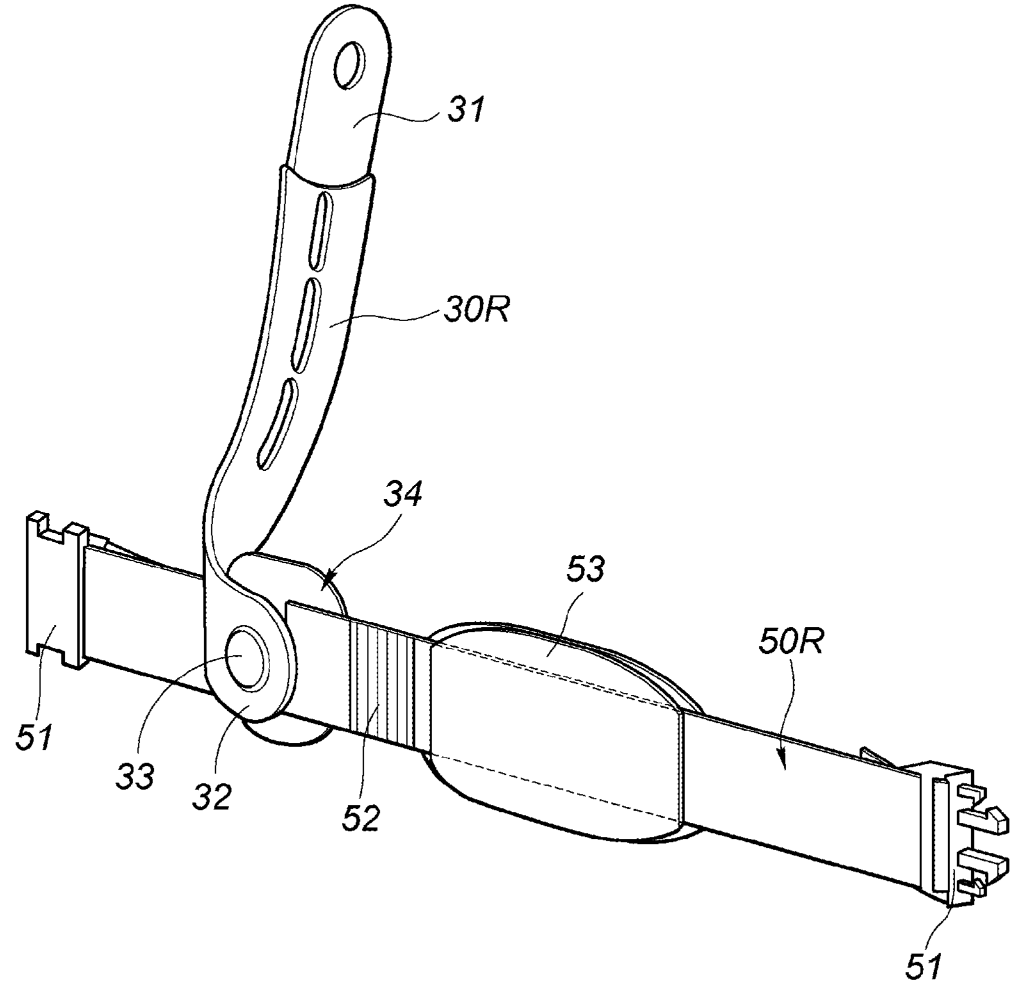
Figure 5:
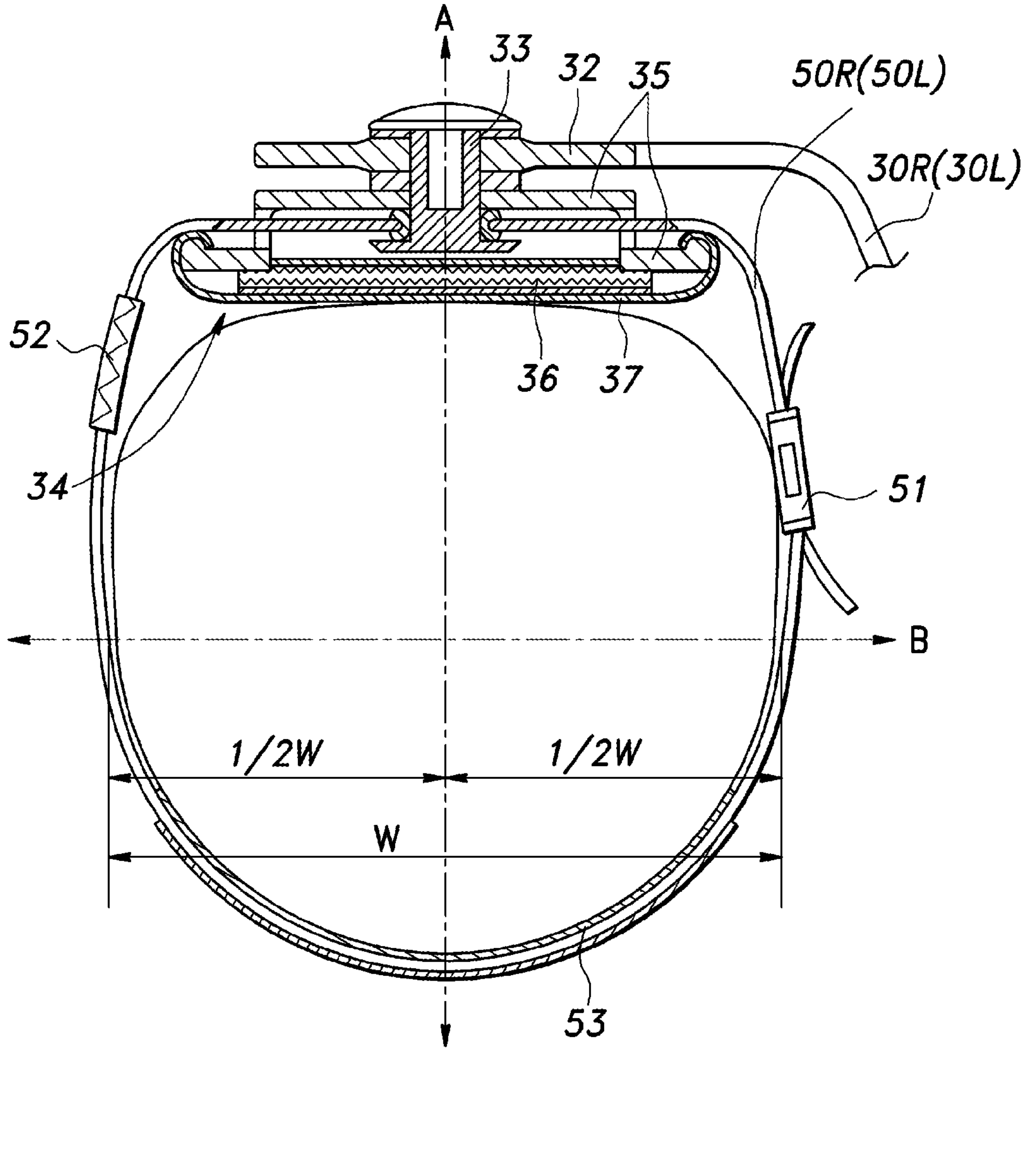

FIG. 4 is a perspective view of the femoral support frame and the flexible belt of the walking assistance device, the flexible belt being shown in a developed state; and FIG. 5 is a bottom plan view of a part of the walking assistance device engaged with the lower part of the femoral part of the user wearing the walking assistance device, with front and back portions of the part of the walking assistance device being shown in cross section taken along line V-V in FIG. 3.

DETAILED DESCRIPTION OF THE PREFERRED EMBODIMENT(S)

A preferred embodiment of the walking assistance device of the present invention will be described in the following with reference to FIGS. 1 to 5.

The walking assistance device of the illustrated embodiment comprises a pelvic frame 10 configured to be detachably worn on a pelvic part or waist part of the user (human being) with a abdominal belt 20 tightened around the pelvic part, a pair of electric motor units (power generators) 14L and 14R, a pair of femoral support frames 30L and 30R and a pair of flexible belts 50L and 50R.

The pelvic frame 10 is formed by molding hard plastic material such as carbon fiber reinforced plastic material, and includes a central part 11 located on a lower back part of the user and a pair of lateral extensions 12 extending from the central part 11 to either side of the pelvic part of the user (or laterally outer side of either hip joint of the user). Therefore, the pelvic frame 10 is provided with the shape of letter-C as seen from above.

From the free end of each lateral extension 12 of the pelvic frame 10 depends a fixed member (motor housing) of each electric motor unit 14L, 14R via a hinge 13. The central part 11 of the pelvic frame 10 is incorporated with an electric unit housing 15 receiving a power source (rechargeable battery) for the electric motor units 14L and 14R, and a controller unit therein.

The hinge 13 is provided with a hinge axis extending horizontally in the fore and aft direction (sagittal axis A) of the user (see FIG. 5). Therefore, each electric motor unit 14L, 14R is suspended on the corresponding side of the pelvic part of the user or outside of the corresponding hip joint of the user, and is allowed to swing around the hinge axis. Therefore, the electric motor units 14L and 14R mounted on the side parts of the user do not constrain or impede the movement of the hip joints of the user.

Each motor unit 14L, 14R includes an electric motor (not shown in the drawings) that receives a supply of electric power from the power source, and is individually controlled by the control unit so as to provide a prescribed assistance force for the movement of the femoral part of the user or for the walking effort of the user.

The side of each electric motor unit 14L, 14R facing the side part of the pelvic part is provided with a pad member 16 incorporated with cushioning material such as foamed material.

The abdominal belt 20 includes a left belt member 20L and a right belt member 20R. An end of each abdominal belt member 20L, 20R is passed through a belt ring 21 pivotally connected to the corresponding side of the central part 11 of the frame 10, and is engaged to an intermediate part of the belt member via an adjustment buckle 22 that allows the length of the belt member to be adjusted. The other end of each abdominal belt member 20L, 20R is passed through a fastening buckle 23 located in a central front part of the belly of the user, and loops back to a belt ring 24 pivotally connected to the corresponding lateral extension 12 of the frame 10. The other end of each abdominal belt member 20L, 20R is then passed through the belt ring 24 and is engaged to an intermediate part of the belt member via an adjustment buckle 25 that allows the length of the belt member to be adjusted.

Therefore, the abdominal belt 20 can be worn by the user to support the pelvic frame 10 at four points by extending in the shape of letter-X without causing any undue load on the pelvic part of the user. As the length of the abdominal belt 20 can be adjusted at each side of the user, the abdominal belt 20 can be adapted to users of various builds and preferences.

Each femoral support frame 30L, 30R consists of a flat bar made of molded hard plastic material such as carbon fiber reinforced plastic material, and comprises a base end 31 (FIGS. 3 and 4) connected to an output end 17 (FIG. 3) of the corresponding electric motor unit 14L, 14R and a free end 32 extending from the base end 31 to a position ahead of a lower femoral part of the user in the case of the illustrated embodiment. Each femoral support frame 30L, 30R is given with a twisted shape by extending along the outer side of the femoral part of the user at the base end 31 thereof and the front side of the femoral part of the user at the free end 32 thereof. In the case of the illustrated embodiment, each femoral support frame 30L, 30R is twisted by an angle of 90 degrees or slightly smaller angle as seen in the horizontal projected plane.

The position ahead of a lower femoral part of the user as used herein means a position corresponding to the central part of the horizontal cross section of a lower femoral part of the user along the frontal axis (lateral axis) B (or the middle point of the width W of the horizontal cross section of the lower femoral part of the user along the frontal axis) at the height corresponding to the free end 32 of the femoral support frame 30L, 30R. As the width W along the frontal axis varies from one person to another, the femoral support frame 30L, 30R may be prepared for an adult person of an average build or may be custom made for each user.

To the free end of each femoral support frame 30L, 30R is attached a front pad member 34 via a pivot pin 33 so as to be rotatable around the sagittal axis of the user. The pivot pin 33 extends in the sagittal axis direction at the middle point of the width W of the horizontal cross section of a lower femoral part of the user (as measured along the frontal axis) at the height corresponding to the free end 32 of the femoral support frame 30L, 30R, and rotatably supports the corresponding front pad member 34 around the central axial line thereof.

The front pad member 34 comprises a base plate 35 made of a material having a suitable stiffness and resiliency such as plastic material and metallic material, a cushion member 36 attached to the base plate 35 and made of cushioning material such as three-dimensional fabric and foamed material, and a surface skin member 37 covering the cushion member 36 and attached to the base plate 35. The surface skin member 37 may be made of leather or PCV sheet. The base plate 35 is directly supported by the pivot pin 33.

To the free end 32 of each femoral support frame 30L, 30R is pivotally attached a flexible belt 50L, 50R via the pivot pin 33 so as to be rotatable around the sagittal axis of the user.

Each flexible belt 50L, 50R is mostly made of fabric, synthetic leather, genuine leather or other flexible material, and is partly made of elastic member 52 such as a rubber belt, and is configured to be wrapped around the lower femoral part of the user in a detachable manner at the height of the free end 32 of the femoral support frame 30L, 30R. The flexible belt 50L, 50R is looped around the entire circumference of the lower femoral part in a detachable and adjustable manner owing to the use of an adjustable buckle 51.

In addition to be fastened by using the buckle 51, each flexible belt 50L, 50R is fastened by using a surface fastener 54, 55 provided thereon.

Each flexible belt 50L, 50R is provided with a rear pad member 53 at the position thereof corresponding to a rear side of a lower femoral part of the user.

In the illustrated embodiment of the walking assistance device, the free end 32 of each femoral support frame 30L, 30R that transmits the walking assistance force generated by the corresponding electric motor unit 14L, 14R to the corresponding femoral part of the user is located in front of the lower femoral part of the user, and is secured to the lower femoral part of the user via the flexible belt that is wrapped around the entire circumference of the lower femoral part of the user at the height of the free end of the femoral support frame 30L, 30R via a front pad member 34, so that the walking assistance force generated by the electric motor unit 14L, 14R is accurately transmitted to the lower femoral part of the user in the direction of the sagittal direction or fore and aft direction of the user without causing any relative movement between them.

As the front pad member 34 is provided on the free end 32 of each femoral support frame member 30L, 30R, the walking assistance force can be imparted to the user without the hard surface of each femoral support frame 30L, 30R engaging the user, and with a comfortable fit.

As each flexible belt 50L, 50R is wrapped around the entire circumference of the femoral part of the user, the contact pressure to the lower femoral part of the user is distributed between the front pad member 34 and flexible belt 50L, 50R. Furthermore, the femoral support frame 30L, 30R made of rigid material is caused to engage the lower femoral part of the user only at the rectus femoris muscle in the front part of the femoral part of the user which undergoes a relatively small deformation in walking as compared to the semitendinosus muscle and biceps femoris muscle which are in the rear part of the femoral part of the user, and the semitendinosus muscle and biceps femoris muscle are simply wrapped around by the flexible belt 50L, 50R so that the user is not subjected to any undue pressure or discomfort. Also, as there is no hard member behind the femoral part of the user, the user wearing the walking assistance device can comfortable sit. In other words, as there is no hard frame or plate behind the femoral part of the user, the user wearing the walking assistance device is enabled to sit in a natural way without experiencing any discomfort.

The length of each flexible belt 50L, 50R can be adjusted as required by using the buckle 51. Thereby, an optimum fastened state can be accomplished by taking into account the personal preference and the build of each particular user. Furthermore, as a part of each flexible belt 50L, 50R is made of elastic member 52 such as a rubber belt, owing to the resilient deformation of the elastic member, the flexible belt 50L, 50R can be worn on the lower femoral part with a favorable fit, and the walking assistance force can be transmitted to the lower femoral part of the user without involving any rattling or shock.

The surface skin member of the front pad member 34 and/or the rear pad member 52 may be made of low friction material such as nylon, polyester or polypropylene fabric sheet, synthetic leather or genuine leather.

In this case, if there is any movement between the user and walking assistance device, each femoral support frame 30L, 30R and each flexible belt 50L, 50R is allowed slip over the surface of the femoral part of the user with a small friction, and this contributes to improving the wearing comfort of the walking assistance device.

Although the present invention has been described in terms of a preferred embodiment thereof, it is obvious to a person skilled in the art that various alterations and modifications are possible without departing from the scope of the present invention which is set forth in the appended claims.

GLOSSARY

10 pelvic frame
14L, 14R electric motor units
20 abdominal belt
30L, 30R femoral support frame
31 base end
32 free end
33 pivot pin
34 front pad member
50L, 50R flexible belt
52 elastic member

The invention claimed is:

1. A walking assistance device for providing a walking assistance force to a femoral part of a user, comprising:

a C-shaped pelvic frame configured to be worn on a back part of the user and to extend on either side of a pelvic part of the user;

a power generator provided on a part of the pelvic frame corresponding to a side of the pelvic part of the user;

a single rigid femoral support frame connected to the power generator, the femoral support frame having a base end connected to an output end of the power generator and a free end extending from the base end to a position adapted to oppose a front part of the femoral part of the user, wherein among the front part of the femoral part of the user and a rear part of the femoral part of the user, which is opposite to the front part of the femoral part of the user, the femoral support frame is configured to oppose only the front part of the femoral part of the user, and a flexible belt attached to the free end of the femoral support frame via a pivot pin and adapted to be releasably worn around a circumference of the femoral part of the user at a height corresponding to that of the free end of the femoral support frame, wherein the femoral support frame is an only rigid support frame connected to the power generator, and the walking assistance device is devoid of a rigid support frame configured to oppose the rear part of the femoral part of the user.

2. The walking assistance device according to claim 1, wherein the flexible belt is rotatably attached to the free end of the femoral support frame so as to be rotatable around a sagittal axis of the user relative to the free end of the femoral support frame.

3. The walking assistance device according to claim 1, wherein a part of the free end of the femoral support frame is provided with a pad member positioned and adapted to abut the front part of the femoral part of the user.

4. The walking assistance device according to claim 3, wherein at least one of the flexible belt and the pad member comprises a surface skin member made of low-friction material.

5. The walking assistance device according to claim 3, wherein the pad member is rotatable relative to the free end of the femoral support frame around a sagittal axis of the user.

6. The walking assistance device according to claim 1, wherein the femoral support frame is made of a rigid plate having a major surface configured to extend along an outer lateral side of the femoral part of the user at the base end of the femoral support frame and along the front part of the femoral part of the user at the free end of the femoral support frame, such that the femoral support frame is configured to form a twisted shape along an outer surface of the femoral part of the user.

7. The walking assistance device according to claim 1, wherein the flexible belt is at least partly made of elastic material.

8. The walking assistance device according to claim 1, wherein the femoral support frame consists of:

a rigid plate having a major surface configured to extend along an outer lateral side of the femoral part of the user at the base end of the femoral support frame and along the front part of the femoral part of the user at the free end of the femoral support frame, such that the femoral support frame is configured to form a twisted shape along an outer surface of the femoral part of the user.

9. The walking assistance device according to claim 8, further comprising:

a pad member provided on the free end of the femoral support frame, the pad member positioned and adapted to abut the front part of the femoral part of the user, and a rear pad member provided on the flexible belt, the rear pad member positioned and adapted to abut the rear part of the femoral part of the user.

10. The walking assistance device according to claim 3, wherein the flexible belt is provided with a rear pad member positioned and adapted to abut the rear part of the femoral part of the user.

11. The walking assistance device according to claim 6, wherein the free end of the femoral support frame is provided with a pad member positioned and adapted to abut the front part of the femoral part of the user, and the flexible belt is provided with a rear pad member positioned and adapted to abut the rear part of the femoral part of the user.

12. A walking assistance device for providing a walking assistance force to first and second femoral parts of a user, comprising:

a C-shaped pelvic frame configured to be worn on a back part of the user and to extend on either side of a pelvic part of the user;

a first power generator provided on a part of the pelvic frame corresponding to a first side of the pelvic part of the user, and a second power generator provided on a part of the pelvic frame corresponding to a second side of the pelvic part of the user, the part of the pelvic frame corresponding to the second side of the pelvic part of the user being substantially opposite to the part of the pelvic frame corresponding to the first side of the pelvic part of the user;

a single rigid first femoral support frame connected to the first power generator, the first femoral support frame having a base end connected to an output end of the first power generator and a free end extending from the base end and adapted to oppose a front part of the first femoral part of the user, wherein among the front part of the first femoral part of the user and a rear part of the first femoral part of the user, which is opposite to the front part of the first femoral part of the user, the first femoral support frame is configured to oppose only the front part of the first femoral part of the user, and a single rigid second femoral support frame connected to the second power generator, the second femoral support frame having a base end connected to an output end of the second power generator and a free end extending from the base end and adapted to oppose a front part of the second femoral part of the user, wherein among the front part of the second femoral part of the user and a rear part of the second femoral part of the user, which is opposite to the front part of the second femoral part of the user, the second femoral support frame is configured to oppose only the front part of the second femoral part of the user; and a first flexible belt attached to the free end of the first femoral support frame via a first pivot pin and adapted to be releasably worn around a circumference of the first femoral part of the user at a height corresponding to that of the free end of the first femoral support frame, and a second flexible belt attached to the free end of the second femoral support frame via a pivot pin and adapted to be releasably worn around a circumference of the second femoral part of the user at a height corresponding to that of the free end of the second femoral support frame, wherein the first femoral support frame is an only rigid support frame connected to the first power generator, the second femoral support frame is an only rigid support frame connected to the second power generator, and the walking assistance device is devoid of a rigid support frame configured to oppose the rear part of the femoral part of the user.

13. The walking assistance device according to claim 12, wherein the first flexible belt is rotatably attached to the free end of the first femoral support frame so as to be rotatable around a sagittal axis of the user relative to the free end of the first femoral support frame, and the second flexible belt is rotatably attached to the free end of the second femoral support frame so as to be rotatable around a sagittal axis of the user relative to the free end of the second femoral support frame.

14. The walking assistance device according to claim 12, wherein a part of the free end of the first femoral support frame is provided with a first pad member positioned and adapted to oppose the front part of the first femoral part of the user, and a part of the free end of the second femoral support frame is provided with a second pad member positioned and adapted to oppose the front part of the second femoral part of the user.

15. The walking assistance device according to claim 14, wherein at least one of the first flexible belt and the first pad member comprises a surface skin member made of low-friction material, and at least one of the second flexible belt and the second pad member comprises a surface skin member made of low-friction material.

16. The walking assistance device according to claim 14, wherein the first pad member is rotatable relative to the free end of the first femoral support frame around a sagittal axis of the user, and the second pad member is rotatable relative to the free end of the second femoral support frame around the sagittal axis of the user.

17. The walking assistance device according to claim 14, wherein the first flexible belt is provided with a first rear pad member positioned and adapted to abut the rear part of the first femoral part of the user, and the second flexible belt is provided with a second rear pad member positioned and adapted to abut the rear part of the second femoral part of the user.

18. The walking assistance device according to claim 12, wherein the first femoral support frame is made of a rigid plate having a major surface configured to extend along an outer lateral side of the first femoral part of the user at the base end of the first femoral support frame and along the front part of the first femoral part of the user at the free end of the first femoral support frame, such that the first femoral support frame is configured to form a twisted shape along an outer surface of the first femoral part of the user, and the second femoral support frame is made of a rigid plate having a major surface configured to extend along an outer lateral side of the second femoral part of the user at the base end of the second femoral support frame and along the front part of the second femoral part of the user at the free end of the second femoral support frame, such that the second femoral support frame is configured to form a twisted shape along an outer surface of the second femoral part of the user.

19. The walking assistance device according to claim 18, wherein the free end of the first femoral support frame is provided with a first pad member positioned and adapted to abut the front part of the first femoral part of the user, the free end of the second femoral support frame is provided with a second pad member positioned and adapted to abut the front part of the second femoral part of the user, the first flexible belt is provided with a first rear pad member positioned and adapted to abut the rear part of the first femoral part of the user, and the second flexible belt is provided with a second rear pad member positioned and adapted to abut the rear part of the second femoral part of the user.

20. The walking assistance device according to claim 12, wherein the first flexible belt is at least partly made of elastic material and the second flexible belt is at least partly made of elastic material.

21. The walking assistance device according to claim 12, wherein the first femoral support frame consists of:

a rigid plate having a major surface configured to extend along an outer lateral side of the first femoral part of the user at the base end of the first femoral support frame and along the front part of the first femoral part of the user at the free end of the first femoral support frame, such that the first femoral support frame is configured to form a twisted shape along an outer surface of the first femoral part of the user, and the second femoral support frame consists of:

a rigid plate having a major surface configured to extend along an outer lateral side of the second femoral part of the user at the base end of the second femoral support frame and along the front part of the second femoral part of the user at the free end of the second femoral support frame, such that the second femoral support frame is configured to form a twisted shape along an outer surface of the second femoral part of the user.

22. The walking assistance device according to claim 21, further comprising:

a first pad member provided on the free end of the first femoral support frame, the first pad member positioned and adapted to abut the front part of the first femoral part of the user, a second pad member provided on the free end of the second femoral support frame, the second pad member positioned and adapted to abut the front part of the second femoral part of the user, a first rear pad member provided on the first flexible belt, the first rear pad member positioned and adapted to abut the rear part of the first femoral part of the user, and a second rear pad member provided on the second flexible belt, the second rear pad member positioned and adapted to abut the rear part of the second femoral part of the user.

* * * * *